United States Patent [19]

Härle

[11] Patent Number: 4,642,093
[45] Date of Patent: Feb. 10, 1987

[54] ASPIRATOR FOR WITHDRAWAL OF SECRETIONS FROM WOUNDS

[76] Inventor: Anton Härle, Drechslerweg 40, D-4400 Münster-Roxel, Fed. Rep. of Germany

[21] Appl. No.: 698,987

[22] Filed: Feb. 7, 1985

[30] Foreign Application Priority Data

Feb. 8, 1984 [DE] Fed. Rep. of Germany ....... 3404382

[51] Int. Cl.⁴ .......................................... A61M 31/00
[52] U.S. Cl. ..................................... 604/54; 604/118; 604/319; 604/404
[58] Field of Search ................. 604/54, 118, 317–321, 604/404; 128/711; 73/426–428; 116/227, 234

[56] References Cited

U.S. PATENT DOCUMENTS

| | | | |
|---|---|---|---|
| 4,178,932 | 12/1979 | Ryder et al. | 604/318 |
| 4,455,140 | 6/1984 | Joslin | 604/317 |

FOREIGN PATENT DOCUMENTS

| | | | |
|---|---|---|---|
| 0066699 | 4/1982 | European Pat. Off. | |
| 0061723 | 10/1982 | European Pat. Off. | 604/318 |
| 1810801 | 6/1970 | Fed. Rep. of Germany | |
| 2820517 | 11/1979 | Fed. Rep. of Germany | |
| 2826650 | 4/1981 | Fed. Rep. of Germany | |
| 2246280 | 10/1973 | France | 604/118 |

Primary Examiner—C. Fred Rosenbaum
Assistant Examiner—Jerome R. Smith, Jr.
Attorney, Agent, or Firm—Peter K. Kontler

[57] ABSTRACT

An aspirator for withdrawal of secretions from wounds has an evacuated vessel wherein the subatmospheric pressure prior to admission of secretions into its interior is maintained at a level of between about 0.8 and 1 bar. The vessel carries indicia denoting (e.g., in percent or in milliliters) the known-in-advance maximum quantity if secretions which can be sucked into the vessel by way of a cannula as well as lesser quantities which accumulate in the vessel while the pressure rises above the predetermined level as a result of admission of secretions.

29 Claims, 1 Drawing Figure

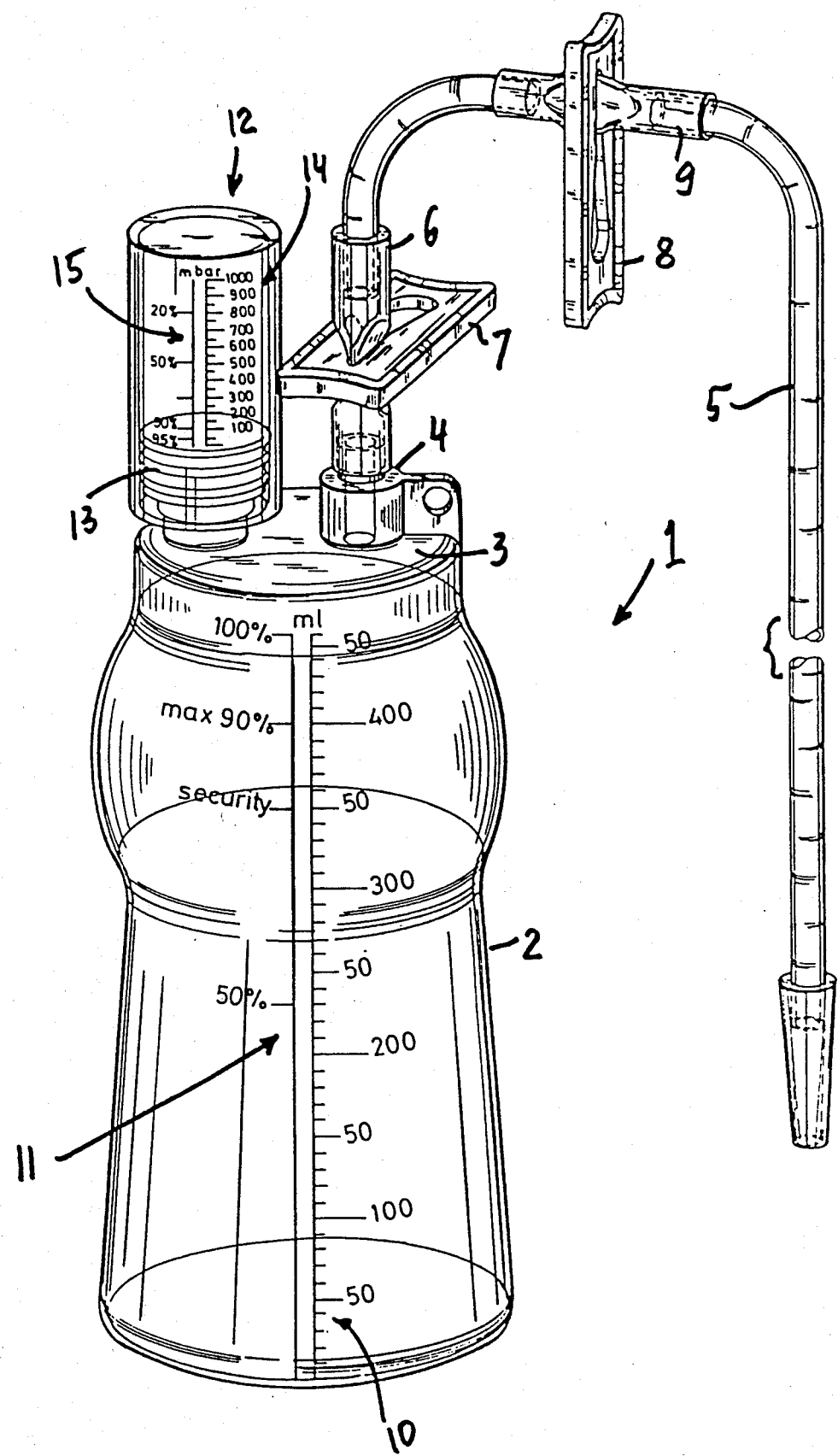

ASPIRATOR FOR WITHDRAWAL OF SECRETIONS FROM WOUNDS

BACKGROUND OF THE INVENTION

The present invention relates to improvements in aspirators for withdrawal of secretions from wounds and for analogous purposes. More particularly, the invention relates to improvements in aspirators of the type wherein a bottle or another suitable vessel has an inlet for attachment of a needle or cannula which can draw secretions from wounds or from cavities of animal bodies due to the pressure differential between the interior of the vessel and the surrounding atmosphere.

Aspirators of the above outlined character can be employed postoperatively for withdrawal of secretions from wounds which are the result of injury or surgery as well as for adaptation of the surfaces bounding the wounds, normally for a period of several (for example, three) days following the operation. As a rule, or at least in many instances, the aspirator comprises a rigid or substantially rigid vessel from which air is withdrawn so that the subatmospheric pressure in its interior is supposed to equal or approximate a preselected value. The vessel is normally of the dispensable type, i.e., it is discarded after a single use, and its inlet is connected to a needle or cannula by way of which secretions are drained from the wound and/or by way of which the wound is drained by suction.

An aspirator of the just outlined character is disclosed, for example, in German Auslegeschrift No. 28 20 517. This aspirator is provided with a pressure indicator which is located at the top of the vessel and whose primary purpose is to indicate whether or not the aspirator is ready for use. In other words, the indicator serves to furnish information denoting to the patient, to the nurse or to the physician that the pressure in the interior of the vessel is below atmospheric pressure, i.e., that the vessel is ready to draw secretions by way of a needle, a cannula or an analogous implement.

In certain presently known aspirators, the means for indicating the pressure in the interior of the vessel include bellows, elastically deformable membranes or reciprocable plungers which can be observed from the outside and whose position relative to a scale or the like denotes the pressure prevailing in the interior of the vessel. A drawback of such pressure indicating devices is that their mobile parts are likely to jam and/or adhere to the adjacent portion of the vessel due to accumulation of condensate in the interior of the vessel and/or as a result of contamination by secretions. Moreover, known indicating devices are merely designed to denote the presence or absence of suction but not the exact subatmospheric pressure (if any) which prevails in the interior of the vessel. In other words, a person observing the position of the bellows, membrane or plunger will merely ascertain that the interior of the vessel is or is not maintained at less than atmospheric pressure but the exact pressure cannot be ascertained at all. Therefore, such person is not in a position to determine whether or not the initial pressure (prior to admission of any secretions into the vessel) matches or approaches the prescribed or optimum value, i.e., whether or not the vessel is indeed capable of accumulating a certain quantity of secretions.

The ability of the aspirator to accumulate secretions depends entirely on the subatmospheric pressure which prevails in the interior of the vessel prior to admission of secretions. Once the pressure has risen to a certain level, the vessel is incapable of drawing additional secretions, i.e., the secretions accumulate in the wound and are likely to cause an enlargement of the wound, hematoma and/or other undesirable phenomena. Moreover, the adaptation of the region surrounding the wound is terminated or interrupted which can lead to infection of the wound. Thus, the inability of a conventional aspirator to indicate whether or not the vessel is capable of accepting additional secretions and/or the maximum quantity of secretions which can be gathered in the vessel constitutes a serious drawback which can have grave consequences if the condition of the aspirator is not monitored continuously or at frequent intervals. The person in charge cannot rely simply on superficial visual observation of the contents of the vessel since the vessel cannot be filled to capacity but rather only as long as the subatmospheric pressure therein is within a certain range, i.e., the secretions can fill only a certain percentage of the overall volume of the vessel.

OBJECTS AND SUMMARY OF THE INVENTION

An object of the invention is to provide a novel and improved aspirator which is constructed and assembled in such a way that the user can ascertain the quantity of gathered secretions in its vessel as well as the ability or inability of the vessel to accept additional secretions.

Another object of the invention is to provide an aspirator which can be used by a patient, a nurse, a physician or any other responsible person as a superior substitute for heretofore known aspirators, especially as concerns the user's ability to ascertain the maximum quantity of secretions which can be gathered in its vessel.

A further object of the invention is to provide a novel and improved aspirator whose vessel is evacuated to an optimum extent for reception of a relatively large quantity of secretions.

An additional object of the invention is to provide a novel and improved vessel for use in the above outlined aspirator.

Still another object of the invention is to provide a novel and improved method of indicating the capacity of the aspirator vessel to accept secretions.

A further object of the invention is to provide a novel and improved method of applying indicia to the vessel of an aspirator or to an information carrier which accompanies the aspirator.

Another object of the invention is to provide novel and improved means for indirectly indicating the pressure which prevails in the vessel of an aspirator.

An additional object of the invention is to provide a novel and improved aspirator which reduces the likelihood of retrograde flow of secretions, of infection, of hematoma and of other undesirable phenomena.

A further object of the invention is to provide an aspirator which can be mass-produced at a low cost.

The invention resides in the provision of an aspirator for withdrawal of secretions from wounds. The aspirator comprises a vessel having a normally sealed inlet for admission of secretions into its interior and means for indicating the maximum quantity of secretions which can enter the vessel by suction when the subatmospheric pressure in the interior of the vessel prior to admission of secretions thereinto matches a predetermined value, preferably between about 0.8 and 1 bar and most preferably between about 0.85 and 0.95 bar.

The indicating means can directly or indirectly furnish information pertaining to the subatmospheric pressure in the vessel. Alternatively, the aspirator can comprise discrete or additional means for indicating the pressure in the interior of the vessel. The means for indicating the maximum quantity of secretions can comprise indicia which are fixedly applied to and are observable from the exterior of the vessel, preferably a vessel at least a portion of which transmits light so that the quantity of secretions which have accumulated in its interior can be observed from the outside. The indicia preferably denote the maximum quantity of secretions which can accumulate in the vessel as well as lesser quantities during various stages of filling of the vessel as the pressure therein rises above (i.e., as the negative pressure therein drops below) the predetermined value in response to admission of secretions into the interior of the vessel. The indicia can denote quantities of secretions in percent and/or in milliliters, and such indicia can be applied in a single color or in two or more different colors either directly on or in the wall of the vessel or on a separate carrier (such as a sheet of paper or the like or a package or another container for the vessel or the entire aspirator). The indicia can denote the maximum quantity of secretions in percent of the overall capacity of the vessel and as a function of the predetermined value of subatmospheric pressure.

The indicia can be designed to denote that quantity of secretions (a) which can enter the vessel by suction when the subatmospheric pressure in the interior of the vessel prior to admission of secretions matches a predetermined value and (b) whose retrograde flow toward the wound is impossible as long as the vessel is not lifted to a level exceeding the level of the wound by more than one meter.

The novel features which are considered as characteristic of the invention are set forth in particular in the appended claims. The improved aspirator itself, however, both as to its construction and the mode of using the same, together with additional features and advantages thereof, will be best understood upon perusal of the following detailed description of certain specific embodiments with reference to the accompanying drawing.

BRIEF DESCRIPTION OF THE DRAWING

The single Figure of the drawing is a perspective view of an aspirator which embodies one form of the invention, a portion of the cannula being broken away and the inlet of the vessel being sealed from the surrounding atmosphere.

DESCRIPTION OF THE PREFERRED EMBODIMENTS

The drawing shows an aspirator 1 which includes an upright vessel 2 consisting of a rigid light-transmitting material (e.g., glass or a transparent or translucent synthetic plastic substance) whose top wall 3 is provided with an inlet 4 for attachment of a cannula 5 serving as a means for directly drawing secretions from a wound following a surgery. The cannula 5 is connected to the inlet 4 by a flexible hose 6 which is sealed by a customary clamp 7. A second clamp 8 seals a second flexible hose 9 which is used to connect two rigid sections of the cannula 5 to each other.

The wall of the main portion of the vessel 2 is provided with indicia in the form of two scales 10 and 11 one of which denotes the quantity of accumulated secretions in milliliters and the other of which denotes the quantity of accumulated secretions in percent. The illustrated vessel 2 is empty, i.e., it is devoid of secretions, and the negative or subatmospheric pressure therein matches or closely approximates a known predetermined value, preferably between about 0.8 and 1 bar, most preferably between about 0.85 and 0.95 bar.

The top wall 3 of the vessel 2 carries a pressure indicating device 12 whose housing communicates with the top portion of the interior of the vessel 2 and contains a deformable bellows 13 having a top wall which can be said to constitute a pointer movable up and down along a scale 14 whose graduations indirectly denote the pressure in the interior of the vessel 2. Thus, and assuming that the maximum pressure in the vessel 2 is 1000 millibar when the vessel does not contain any secretions, the top wall of the bellows 13 in the indicating device 12 is adjacent to the 0-millibar graduation. When the top wall of the bellows 13 is adjacent to the 100-millibar graduation of the scale 14, the pressure in the vessel 2 equals 900 millibar, and so forth. Another scale 15 on the light-transmitting housing of the indicating device 12 furnishes the same information as the scale 14 but in percent. Thus, the graduations of the scale 15 denote in percent the prevailing negative pressure in the interior of the vessel 2 relative to the predetermined and known negative pressure when the vessel 2 is still empty.

The graduations or indicia of the scales 10, 11 and/or 14, 15 can be furnished in a single color (e.g., black or red) or in two or more colors (e.g., red and black). By way of example, the graduations of the scale 10 may be applied directly to the wall of the vessel 2 in black color, and the graduations of the scale 11 can be applied directly to the wall of the vessel 2 but in another (e.g., red) color. The same holds true for the graduations of the scales 14 and 15. It is also possible to provide the scale 10 on the wall of the vessel 2 and to provide a reproduction of the scale 10 and the scale 11 on a carrier (e.g., a sheet of paper) which is separate from the vessel 2 but is furnished therewith so that the user of the aspirator 1 can ascertain the quantity of accumulated secretions by looking at the scale 10 on the vessel 2 and such user can also ascertain the percentage of the maximum quantity that can be accommodated in the vessel 2 by looking at the accompanying carrier which is provided with the scales 10 and 11. Alternatively, the carrier can be simply provided with information denoting that 50 milliliters of secretions which accumulate in the vessel 2 amount to 10 percent of maximum quantity which can be accumulated in the vessel, that 100 milliliters constitute 20 percent of such maximum quantity and so forth. It is equally possible to provide the wall of the vessel 2 only with the scale 11 and to provide the scales 10 and 11 (e.g., next to each other as shown in the drawing) on the accompanying carrier.

By way of example, if the maximum value of negative pressure in an evacuated (and still unused) vessel 2 is 0.3 bar, the vessel can be filled with secretions to 30 percent of its overall capacity; if the maximum value of negative pressure is 0.5 bar, the vessel can be filled to 50 percent of its maximum capacity; and the vessel can be filled to 90 percent of its maximum capacity if the maximum value of the negative pressure in its interior is 0.9 bar. These are just a few examples of negative pressures which can be selected by the manufacturer of the improved aspirator.

Referring again to the drawing, the scale 11 includes an indicium or graduation which is denoted by the legend "security" and is intended to denote to a user that it is advisable to replace the vessel when its interior is filled with secretions to such level. Another graduation of the scale 11 denotes the maximum quantity of secretions which can be accumulated in the interior of the vessel 2. The level of the graduation labelled "security" is preferably selected in such a way that the user of the aspirator is assured that no retrograde flow of secretions into the wound can take place if the vessel is not overfilled with secretions (above the just discussed graduation of the scale) and is not lifted to a level more than one meter above the level of the wound.

Instead of applying some or all of the indicia to the wall of the vessel 2 and/or to the aforediscussed sheet-like carrier, some of these indicia can be applied to the container in which the aspirator is supplied to a hospital, a senior citizens' home, a sanitarium, an infirmary, a field hospital, a medical faculty, a first aid station or another institution which utilizes aspirators.

An important advantage of the improved aspirator is that it enables the user to ascertain the maximum quantity of secretions which can be gathered in the vessel 2 as well as other quantities (less than maximum quantity) which can still be admitted into the vessel after the pressure therein has departed from the maximum value of negative pressure as a result of admission of some secretions into the interior of the vessel. Thus, the user of the improved aspirator is in a position to know that, due to the fact that the initial value of negative pressure matches a preselected value (e.g., 0.9 bar), the vessel 2 can accept a certain predetermined maximum quantity of secretions. Suction which is applied to the wound by way of the cannula 5 or another suitable implement is to draw together the surfaces bounding the wound, to promote the flow of secretions from the wound toward the interior of the vessel, and to eliminate the danger of retrograde flow of secretions into the wound when the vessel is held at a level above the wound which is a situation that cannot be excluded when the aspirator is in use. As mentioned above, the initial value of negative pressure in the vessel can be selected in such a way that, as long as the vessel is not filled to a particular level (of the graduation labelled "security" on the wall of the vessel 2 which is shown in the drawing), no retrograde flow of secretions will take place if the vessel is not lifted to a level more than one meter above the level of the wound.

The provision of the improved indicating means on the vessel 2, on an accompanying sheet-like carrier and/or on the wrapper or package for the vessel eliminates the following problems which inherently arise when using conventional aspirators without such indicia. The user of the improved aspirator can ascertain at a glance that, due to the selected initial value of negative pressure in the vessel (prior to admission of any secretions into its interior), the vessel can accept a certain maximum quantity of secretions as well as that, in actual use (when the vessel already contains a certain quantity of secretions), the aspirator can still withdraw a certain additional quantity of a liquid or other flowable substance from a wound into which the cannula 5 extends. The user of a conventional aspirator cannot ascertain whether or not the vessel can accept additional quantities of secretions because such conventional aspirator does not indicate the maximum quantity which can enter the interior of the vessel by suction. Thus, and if the user of a conventional aspirator presumes that the vessel is filled to say 50 percent and leaves the vessel attached to the wound, the vessel is likely to have already received the maximum quantity of secretions which can enter its interior by suction so that no additional secretions are being withdrawn from the wound. Such problem is avoided by the simple expedient of providing the improved aspirator with means for indicating the maximum quantity of secretions which can be sucked into the vessel whereby such indications indirectly denote the negative pressure in the vessel. Furthermore, and as shown in the drawing, the improved aspirator can be provided with an additional indicating device 12 which can be observed by the user to ascertain whether or not the initial value of negative pressure in the vessel equals or approximates the advertised or asserted value, e.g., between about 0.8 and 1 bar, preferably between about 0.85 and 0.95 bar.

The scale 10, 11, 14 and/or 15 can be etched into or otherwise formed in the wall of the vessel 2 and/or in the housing of the indicating device 12. Alternatively such scales can be adhesively secured to the vessel 2 and/or the housing of the indicating device as long as their indicia are fixed (i.e., as long as they do not move with the level of accumulated secretions analogously to a bellows, membrane or plunger which is being displaced by the material entering the vessel). When the vessel 2 (wherein the initial negative pressure is between about 0.8 and 1 bar) is filled with secretions to a maximum extent, the negative pressure in the vessel is normally between 0 and 0.2 bar. If the initial negative pressure is between about 0.85 and 0.95 bar, the pressure when the vessel has received the maximum quantity of secretions is between 0.15 and 0.05 bar.

Selection of a relatively high initial subatmospheric pressure is desirable and advantageous on several grounds. Thus, the vessel 2 can be filled to between 80 and 95 percent of its overall capacity. Also, the vessel can always be filled to the indicated extent, i.e., the maximum quantity of secretions which can be sucked into the vessel invariably matches the indicated maximum quantity which means that requisite suction prevails in the vessel until the very moment when it has received the maximum quantity of secretions. Still further, suction does not fluctuate within a wide range while secretions flow into the vessel which ensures a uniform or constant adaptation of the surfaces bounding the wound.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. An aspirator for withdrawal of secretions from wounds, comprising an evacuated vessel having a normally sealed inlet for admission of secretions into its interior; and means for indicating the maximum quantity of secretions which can enter the vessel by suction when the subatmospheric pressure in the interior of the vessel prior to admission of secretions thereinto matches a predetermined value.

2. The aspirator of claim 1, further comprising means for indicating the pressure in the interior of said vessel.

3. The aspirator of claim 1, wherein said indicating means comprises indicia fixedly applied to and observable from the exterior of said vessel.

4. The aspirator of claim 3, wherein at least a portion of said vessel transmits light so that the quantity of secretions in its interior can be observed from the outside.

5. The aspirator of claim 1, wherein said indicating means includes indicia applied to said vessel and denoting said maximum quantity as well as lesser quantities during various stages of filling of the vessel as the pressure therein rises above said predetermined value in response to admission of secretions into its interior.

6. The aspirator of claim 5, wherein said indicia denote quantities of secretions in percent.

7. The aspirator of claim 5, wherein said indicia denote quantities of secretions in milliliters.

8. The aspirator of claim 1, wherein said indicating means includes colored indicia.

9. The aspirator of claim 1, wherein said indicating means comprises indicia in a plurality of different colors.

10. The aspirator of claim 1, wherein said vessel includes a wall and said indicating means comprises indicia provided in said wall.

11. The aspirator of claim 1, wherein said indicating means comprises a carrier separate from said vessel and indicia provided on said carrier.

12. The aspirator of claim 11, wherein said carrier includes a sheet and said indicia denote said maximum quantity in percent of the overall capacity of said vessel and as a function of said predetermined value of subatmospheric pressure.

13. An aspirator for withdrawal of secretions from wounds, comprising an evacuated vessel having a normally sealed inlet for admission of secretions into its interior; and means for indicating that quantity of secretions (a) which can enter the vessel by suction when the subatmospheric pressure in the interior of the vessel prior to admission of secretions thereinto matches a predetermined value, and (b) whose retrograde flow toward the wound is impossible as long as the vessel is not lifted to a level exceeding the level of the wound by more than one meter.

14. The aspirator of claim 13, further comprising means for indicating the pressure in the interior of the vessel.

15. The aspirator of claim 13, wherein said indicating means comprises indicia fixedly applied to and observable from the exterior of said vessel.

16. The aspirator of claim 15, wherein at least a portion of said vessel transmits light so that the quantity of secretions in its interior can be observed from the outside.

17. The aspirator of claim 13, wherein said indicating means comprises a carrier separate from said vessel and indicia provided on said carrier.

18. The aspirator of claim 17, wherein said carrier comprises a sheet and said indicia denote said quantity in percent of the overall capacity of said vessel and as a function of said predetermined value of subatmospheric pressure.

19. The aspirator of claim 13, wherein said indicating means includes indicia applied to said vessel and denoting said quantity as well as other quantities of secretions in the vessel during various stages of filling of the vessel as the pressure therein rises above said predetermined value in response to admission of secretions into its interior.

20. The aspirator of claim 19, wherein said indicia denote quantities of secretions in percent.

21. The aspirator of claim 19, wherein said indicia denote quantities of secretions in milliliters.

22. The aspirator of claim 13, wherein said indicating means includes colored indicia.

23. The aspirator of claim 13, wherein said indicating means comprises indicia in a plurality of different colors.

24. An aspirator for withdrawal of secretions from wounds, comprising an evacuated vessel having a normally sealed inlet for admission of secretions into its interior; and means for furnishing information pertaining to the subatmospheric pressure in the interior of said vessel, including means for indicating the maximum quantity of secretions which can enter the vessel by suction when the subatmospheric pressure in the interior of the vessel prior to admission of secretions thereinto matches a predetermined value.

25. The aspirator of claim 24, wherein said indicating means includes indicia one of which denotes said maximum quantity in percent.

26. The aspirator of claim 24, wherein said indicating means includes indicia one of which denotes said maximum quantity in milliliters.

27. The aspirator of claim 24, wherein said indicating means comprises colored indicia.

28. The aspirator of claim 24, wherein said indicating means comprises indicia in a plurality of different colors.

29. The aspirator of claim 24, wherein said vessel includes a wall and said indicating means comprises indicia applied to said wall.

* * * * *